(12) United States Patent
Franklin et al.

(10) Patent No.: US 9,778,152 B2
(45) Date of Patent: Oct. 3, 2017

(54) CELL COLLECTING APPARATUS AND METHOD OF USE

(71) Applicant: The Regents of the University of Colorado, a body corporate, Denver, CO (US)

(72) Inventors: Wilbur Franklin, Denver, CO (US); Aaron Lieberman, Littleton, CO (US); Mark Palmer, Elizabeth, CO (US); Willem Berglund, Santa Barbara, CA (US); Stephen DeMars, Englewood, CO (US); Andrew Hanuszek, Smithtown, NY (US); Dara Aisner, Denver, CO (US); Qing Ren, Denver, CO (US); Eric Kelso, Erie, CO (US)

(73) Assignee: The Regents of the University of Colorado, Denver, CO (US)

( * ) Notice: Subject to any disclaimer, the term of this patent is extended or adjusted under 35 U.S.C. 154(b) by 99 days.

(21) Appl. No.: 14/397,855

(22) PCT Filed: Apr. 25, 2013

(86) PCT No.: PCT/US2013/038284
§ 371 (c)(1),
(2) Date: Oct. 29, 2014

(87) PCT Pub. No.: WO2013/165813
PCT Pub. Date: Nov. 7, 2013

(65) Prior Publication Data
US 2015/0111242 A1    Apr. 23, 2015

Related U.S. Application Data

(60) Provisional application No. 61/640,676, filed on Apr. 30, 2012, provisional application No. 61/757,366, filed on Jan. 28, 2013.

(51) Int. Cl.
  *A61B 10/00* (2006.01)
  *G01N 1/28* (2006.01)
  *G01N 1/04* (2006.01)
  *A61B 10/02* (2006.01)

(52) U.S. Cl.
  CPC ............ *G01N 1/286* (2013.01); *G01N 1/04* (2013.01); *A61B 10/0283* (2013.01); *G01N 2001/2873* (2013.01)

(58) Field of Classification Search
  CPC ................................................. G01N 1/286
  See application file for complete search history.

(56) References Cited

FOREIGN PATENT DOCUMENTS

EP         1639947      *  3/2005
EP         1639947 A1   *  3/2006   ......... A61B 10/0233

* cited by examiner

*Primary Examiner* — Jyoti Nagpaul
(74) *Attorney, Agent, or Firm* — Don D. Cha; Hamilton DeSanctis & Cha, LLP

(57) ABSTRACT

The present invention provides an apparatus and method for microdissecting a biological sample. In particular, apparatuses of the invention include a cell collecting device 100 that is operated by a pneumatic device 200. In one particular embodiment, apparatuses of the invention are used for collecting and transferring cell sample to and from cell collecting device 100.

13 Claims, 4 Drawing Sheets

CELL COLLECTING APPARATUS AND METHOD OF USE

CROSS-REFERENCE TO RELATED APPLICATIONS

This application claims the priority benefit of U.S. Provisional Application Nos. 61/640,676, filed Apr. 30, 2012, and 61/757,366, filed Jan. 28, 2013, all of which are incorporated herein by reference in their entirety.

STATEMENT REGARDING FEDERALLY FUNDED RESEARCH

This invention was made with government support under grant number CA058187 awarded by the National Institutes of Health. The government has certain rights in the invention

FIELD OF THE INVENTION

The present invention relates to a microdissection apparatus and method for microdissecting a biological sample.

BACKGROUND OF THE INVENTION

In pathology and other cell analysis, it is generally desirable to isolate substantially only the specific cell sample from the biological sample, for example, to perform a DNA analysis and the like. Such selective isolation of desired cell sample allows a more accurate analysis without a significant contamination from other none desirable cells.

Conventional methods are expensive, labor intensive and/or unable to provide the desired cell sample in a suitable concentration for analysis. In addition, some conventional cell extraction methods are slow and/or unsanitary. One example of conventional cell extraction method involves using a mouth pipette to aspirate the desired cell sample from a glycerol covered slide and blowing the sample into an appropriate test tube. The glycerol acts as an inert medium that helps transport the cell sample into the pipette. This method creates the risk of contaminating the patient sample with operator cells and of inadvertently aspirating potentially hazardous patient cellular material into the mouth of the operator.

Another conventional method for extracting the cell sample uses a scalpel and ethanol. This method is generally more tedious and required much greater skill and practice in order to perfect. Because of the small size of the cells, the movements of the scalpel require great precision. Such precision requirement makes this method an art form that is difficult to master and creates the need for a method to cleanly remove cells that have been dislodged from the microdissected slide.

Majority of conventional methods for obtaining a desirable cell sample for analysis from a tissue include fixing the tissue section or sample on a sample immobilizing base having a film attached thereto (e.g. a coated slide glass) and cutting a desired area of the film by tracing a contour of the desired area on the tissue sample. Some conventional methods use a laser light to detach the desired area from the underlying immobilizing matrix and then transfer detached target cells to a second adherent surface from which they are washed for molecular analysis. This method is also technically challenging. When detaching the desired area using a laser light by tracing a contour of the desired cell sample area of a tissue section, the tissue section tends to deform during dissection due at least in part from a pressure generated by evaporation of the sample itself or a stress at an uncut part. Therefore, it is difficult to correctly cut the desired area even with a sophisticated and precise device like a laser, if the tissue section is particularly a deformable biological sample. Moreover, the DNA yield for the amount of time spent and the complicated equipment required is low. In addition, training requirements to master the laser capture device are considerable and the instrument must be adequately maintained by specialized personnel. Furthermore, laser equipment is often expensive and requires a relatively high maintenance.

For small samples that are increasingly being used to guide targeted treatments it is especially important to maximize efficiency of tumor cell collection, smaller amounts of DNA tend to amplify artifactual DNA base alterations that are an inevitable accompaniment of tissue processing methods conventionally used in clinical practice. Multiple sections may need to be dissected in order to maximize DNA yield which may be difficult to achieve with conventional methods and laser capture methods.

Accordingly, there is a need for an apparatus that is more cost effective and easier to use for collecting a desired cell sample from a tissue sample. In addition, there is a need for a simple apparatus and method that can maximize the number of tumor cells that can be harvested from a given tissue section.

SUMMARY OF THE INVENTION

Some aspects of the invention provide an apparatus for collecting a desired cell sample from a tissue section or sample without using a laser to cut the desired cell sample. In some embodiments, apparatuses of the invention are operated pneumatically for collecting a desired cell sample from the tissue section.

Other aspects of the invention provide methods for collecting a desired cell sample from a tissue sample for analysis. Such methods generally include identifying a desired cell sample from a tissue sample using a microscope; and obtaining the desired cell sample for analysis from the tissue sample using a cell collecting device disclosed herein. Typically, such methods include observing the tissue sample with a microscope while collecting the desired cell sample. In some embodiments, the desired cell sample is collected by contacting the desired cell sample with the cell collecting device disclosed herein and aspirating the desired cell sample into the cell collecting device. Generally, the desired cell sample is removed from the tissue sample and substantially simultaneously collected using the cell collecting device.

While any type of microscope can be used that allows the user to observe the tissue sample while operating the cell collecting device, for economical reasons generally a dissecting light microscope is used to observe the tissue sample during cell collecting process. In some embodiments, methods of the invention also include transferring the collected cell sample from the cell collecting device to a cell preparation vessel. Typically, transfer of the collected cell sample to the cell preparation vessel includes changing the cell collecting device from the aspirating mode to the expelling mode. Because the cell collecting device of the invention is operated pneumatically, such change in the setting can be achieved by switching the cell collecting device from vacuum (i.e., aspirate) mode to high pressure mode (e.g., higher pressure relative to the ambient pressure to allow expelling of the cell sample within the cell collecting device to be expelled pneumatically).

In one particular aspect, the invention provides an apparatus for collecting a cell sample from a tissue sample, said apparatus comprising:

a cell sample collecting device comprising a cell collecting element, wherein said cell collecting element comprises a cell collecting orifice and a pneumatic connector orifice, and wherein said cell collecting orifice is adapted for aspirating and expelling a cell sample into and from said cell collecting element;

a pneumatic connector comprising a first orifice and a second orifice, wherein said first orifice of said pneumatic connector is removably attached to said pneumatic connector orifice of said cell collecting element;

a pneumatic device operatively connected to said second orifice of said pneumatic connector; and a control unit operatively connected to said pneumatic device such that said pneumatic device provides means for aspirating or expelling the cell sample into or from said cell collecting element.

In some embodiments, the cell sample collecting device further comprises a guide element adapted to aid in positioning said cell sample collecting element to be removably attached to said pneumatic connector. The cell sample collecting device can further include a housing that encases or protects at least a portion of the cell sample collecting element. Such housing can be a single piece or a multiple piece element. In some particular embodiments, the control unit is located within the housing.

The cell collecting element can be made from any suitable material such as plastic, steel, glass, or a combination thereof. For economical reasons and ready availability, in some instances the cell collecting element comprises a pipette. The glass pipettes are well known to one skilled in the art and are routinely used in scientific laboratories.

In some embodiments, the cell collecting device is attached to a stand that comprises a base unit and an arm unit. This allows the cell collecting device to be fixed to the stand and allows one to keep the device from being contaminated from a surface of the work area when not in use. Alternative, a separate stand can be provided that allows the user to place the cell collecting device when not in use. In some cases, the arm unit of the stand comprises a hinge. This hinge allows the user to move the cell collecting device in various directions and distances.

Yet in other embodiments, the control unit can also include a variable control for adjusting the cell sample aspiration force, cell sample expelling force, or both. In this manner, the amount of force exerted by the cell collecting element can be adjusted as appropriate. Such adjustability allows the user to use a variety of different cell collecting element.

Another aspect of the invention includes a method for obtaining a cell sample for analysis from a tissue sample using the apparatus described herein. In some embodiments, such method includes:

identifying a cell sample to be analyzed from a tissue sample; and obtaining the cell sample to be analyzed using an apparatus described herein.

In some embodiments, said step of identifying the cell sample to be analyzed comprises observing the tissue sample using a microscope. While any type of microscope can be used, generally a dissecting light microscope is used to observe the tissue sample.

Yet in other embodiments, said step of obtaining the cell sample comprises:

contacting the cell collecting element with the cell sample to be analyzed;

aspirating the cell sample into said cell collecting element using said pneumatic device; and expelling the collected cell sample from said cell collecting element into a cell sample collecting vessel.

The method of invention can also include the step of adjusting the control unit after said step of aspirating the cell sample into said cell collecting element such that said pneumatic device provides a positive pressure within said cell collecting element, thereby expelling the collected cell sample from said cell collecting element. In this manner, the collected cell sample can be transferred from the cell collecting element to a cell preparation vessel or to a glass slide directly. As stated above, typically, transfer of the collected cell sample to the cell preparation vessel comprises increasing the pressure within the cell collecting element. The increased pressure within the cell collecting element relative to the ambient pressure causes the collected cell sample to be transferred or expelled from the cell collecting element to the cell preparation vessel or other suitable vessels. The transferred cell sample can then be prepared for analysis, if necessary, and is analyzed.

Typically, the cell collecting element is capable of removing and collecting the cell sample simultaneously.

DETAILED DESCRIPTION OF THE INVENTION

The present invention will now be described with regard to the accompanying drawings which assist in illustrating various features of the invention. In this regard, the present invention generally relates to apparatuses for collecting a cell sample from a tissue sample and methods for using the same. One particular embodiment of a desired cell sample collecting apparatus is generally illustrated in FIG. 1, which is provided for the sole purpose of illustrating the practice of the present invention and which does not constitute limitations on the scope of the present invention.

Apparatuses and methods of the invention can be used in a variety of applications such as pathology, tissue analysis, tumor cell enrichment (e.g., for mutational and other molecular endpoints), and other cell sample collection. Particularly useful application for the apparatuses and methods of the invention is in pathology where a cell sample is collected for analysis. In pathology application, the tissue section (or sample) is obtained from a subject and a particular cell(s) are analyzed, e.g., for abnormalities, malignancy, cancer, etc. As used herein the terms "subject" and "patient" are used interchangeable and refer to an animal, typically a mammal such as human, primate, equine, feline, canine, bovine, rabbit, mouse, pig, etc. Often the subject is human.

While apparatuses and methods of the invention can be used in a wide variety of applications, for the sake of clarity and brevity, the invention will now be described in reference to use in pathology. As generally stated above, in pathology a tissue sample is often obtained for analysis to determine a wide variety of medical conditions, abnormalities and/or a cause of death. The obtained tissue sample is often stained and fixed, for example, using formaldehyde and paraffin or the like. Methods for staining and fixing a tissue section are well known to one skilled in the art.

Figure 1:
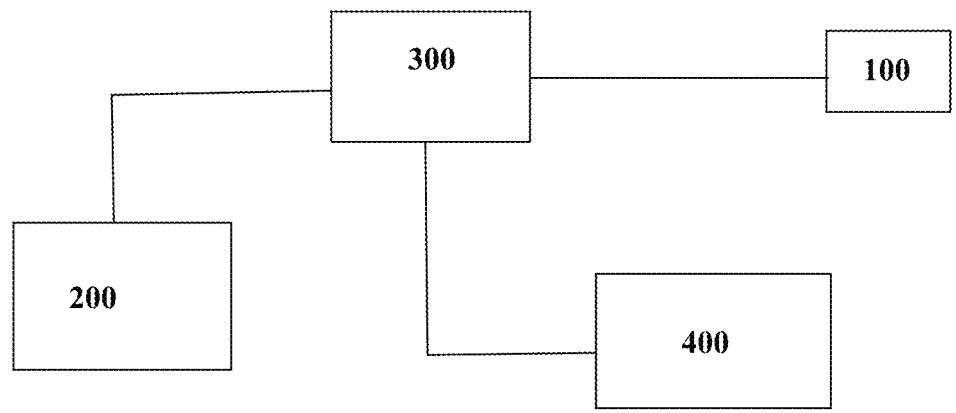
FIG. 1 is an overall schematic illustration of one particular embodiment of the apparatus for collecting cell sample.
Figure 2:
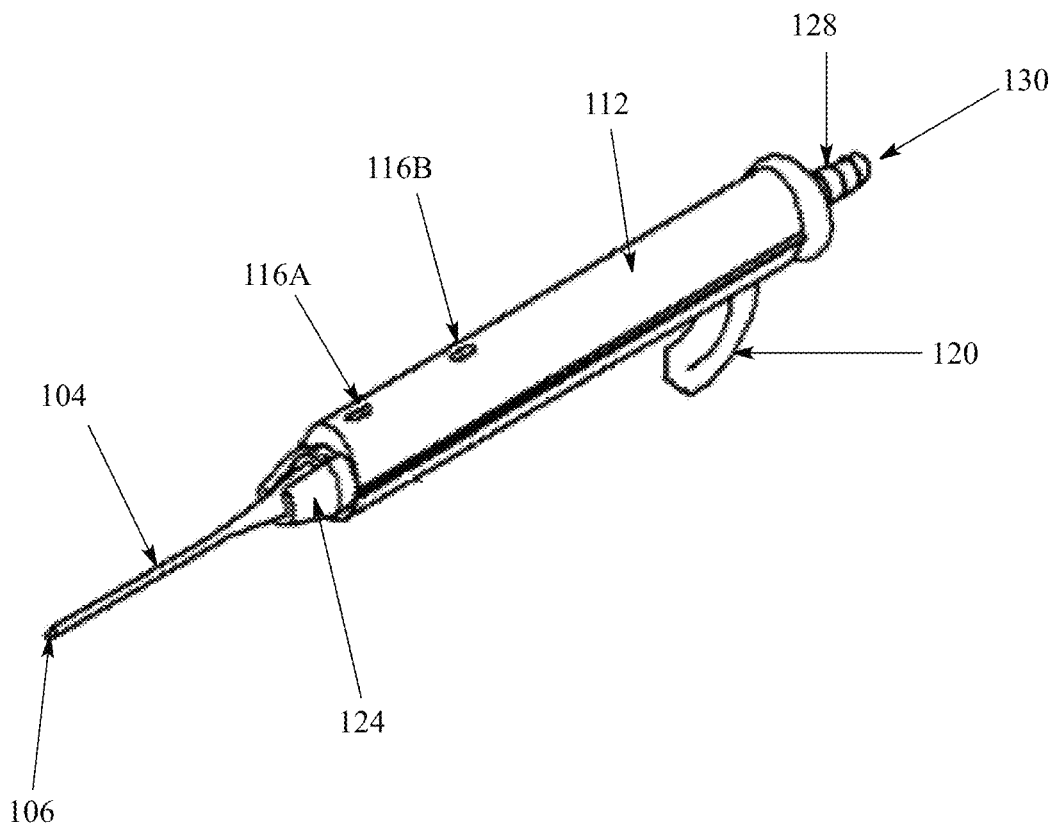
FIG. 2 is a schematic illustration of one particular embodiment of a cell collecting device of the invention.
Figure 3:
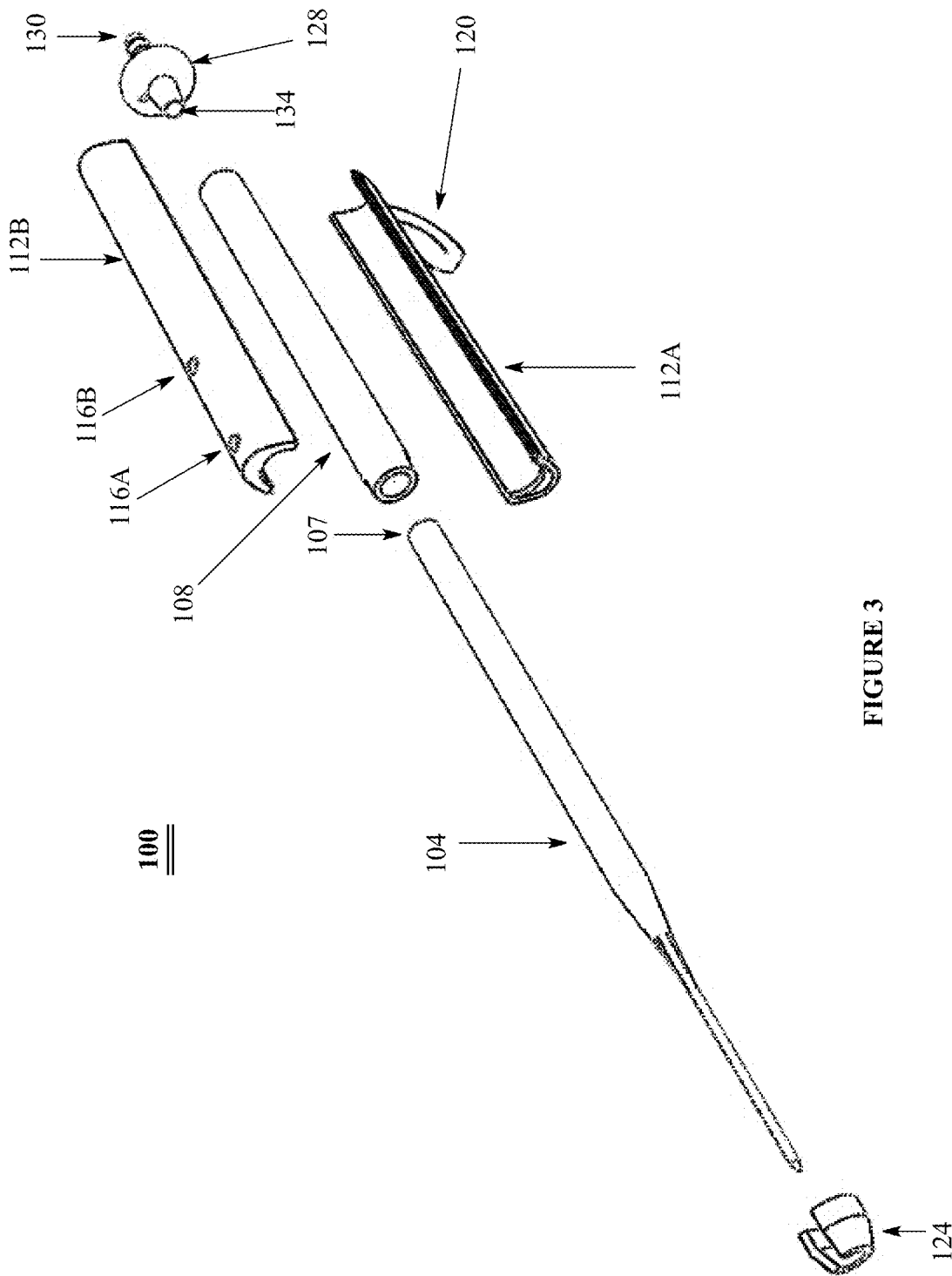
FIG. 3 is an exploded view of a cell collecting device.

Referring to FIG. 1, in one particular embodiment of the invention, the apparatus for collecting cell sample includes a cell collecting device 100, a pneumatic device 200, a power unit 300, and a control unit 400. It should be appreciated that one or more elements can be combined into a single unit. For example, the control unit 400 can be present within the cell collecting device 100, and the pneumatic device 200 and the power unit 300 can be made from a single unit. It should also be appreciated that like numbered item in different figures represents the same item. While not shown, the apparatus can also include a microscope to observe the tissue sample and identify the desired cells for collection. Typically a light microscope, and often a dissecting light microscope is used for this purpose. In use, the stained and fixed tissue sample is typically placed on a slide to allow the user to observe the tissue sample, for example, using a microscope as discussed above. The stained tissue sample slide is typically flooded with or placed in a solution such as glycerin. Under direct observation with the microscope, the desired cell sample is collected with a cell collecting device 100. Cell collecting device 100 can include any cell collecting element 104 that can be used to obtain the desired cell sample from the tissue sample. Exemplary cell collecting elements 104 include, but are not limited to, pipette, syringe, finely tipped scalpel and the like.

Generally, as one observes the tissue sample under a dissecting light microscope, one contacts or "scrapes" the cell sample of interest, i.e., the "desired cell sample," using the cell collecting element 104. This scraping causes the cell sample to be separated from tissue sample and freed from the underlying glass slide. When cell collecting element 104 is under reduced pressure (relative to the ambient pressure, i.e., in an aspiration mode), the pressure differential causes the separated cell sample to enter cell collecting element 104. Once a sufficient amount of the cell sample is obtained, one can transfer the collected cell sample to a cell sample preparation vessel or a cell sample storage vessel (not shown). Transfer of the collected cell sample from cell collecting element 104 to cell sample preparation vessel or the glass slide can be achieved by increasing the pressure within cell collecting element 104 (i.e., by using the control unit 116 to place the cell collecting element 104 in expel mode). This increase in pressure within cell collecting element 104 forces the collected cell sample out of cell collecting element 104 and into cell sample preparation vessel or the cell sample observation vessel (e.g., a glass slide).

Cells can be collected using any suitable fluid, typically glycerin. Other exemplary fluids suitable for transferring collected cells to sample preparation or cell observation vessel include, but are not limited to, gases such as ambient air, nitrogen, helium, argon, and liquids such as saline solution, water, other buffer solutions, organic solvents such as dimethylsulfoxide (DMSO), dimethylformamide (DMF), alcohol (e.g., ethanol), acetone, ether, tetrahydrofuran (THF), etc. When a liquid is used to transfer the collected sample cell from cell collecting element 104 to cell sample preparation or observation vessel, often a suitable solvent is used. Typically, however, ambient gas is used to transfer the cell sample from cell collecting element 104 to cell sample preparation or observation vessel.

In some embodiments, apparatuses of the invention also include a pneumatic device 200 that is operatively connected to cell collecting device 100. Pneumatic apparatus 200 operates cell collecting device 100 such that the desired cell sample is collected within cell collecting element 104 and is transferred to cell sample preparation or observation vessel. In one particular embodiment, pneumatic apparatus 200 comprises a plurality of three-way valves (see FIG. 4) and a vacuum pump.

Figure 4:
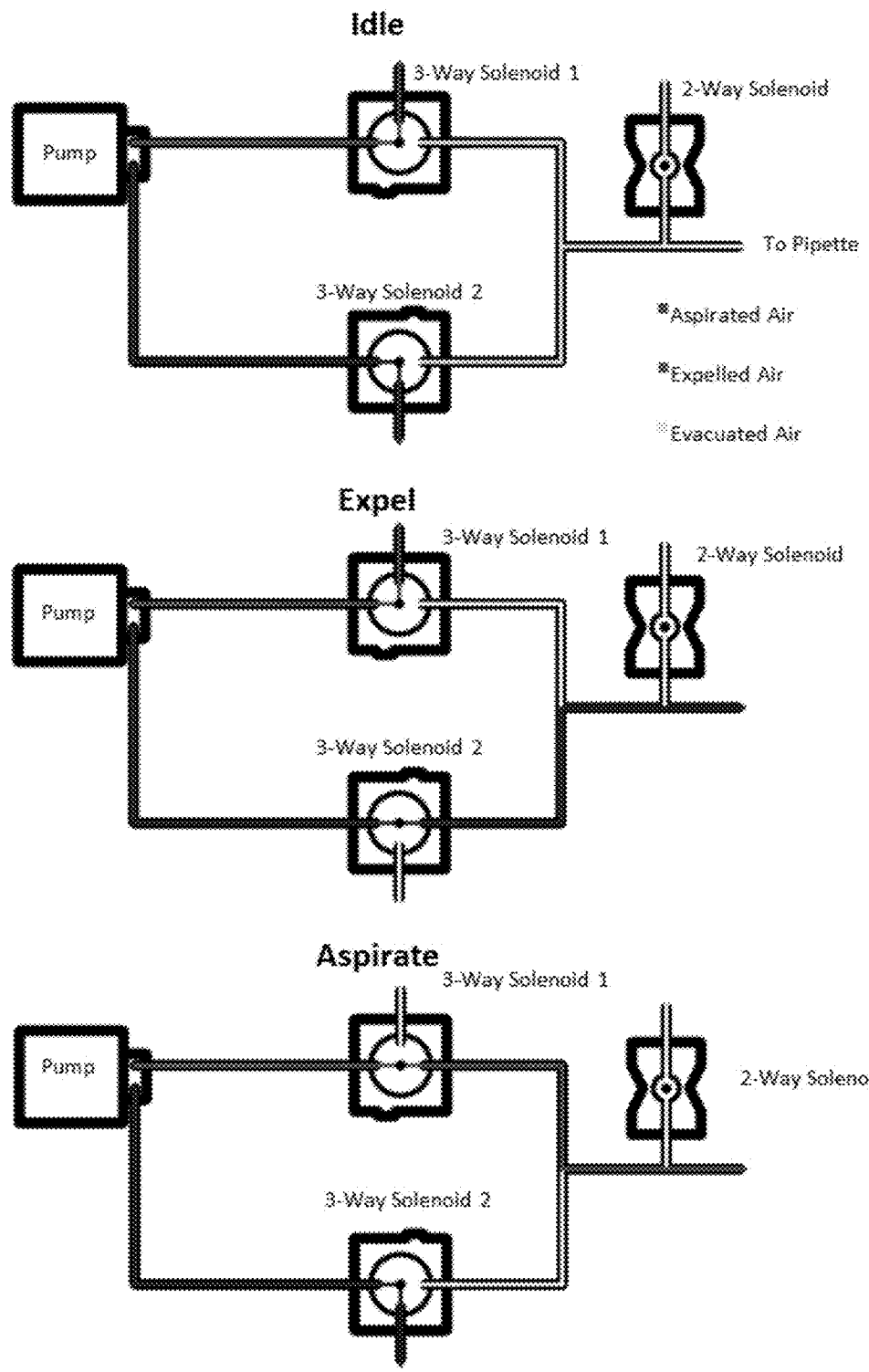
FIG. 4 is a power unit flow diagram.

Inlet port of pneumatic apparatus 200 is operatively connected to cell collecting device 100. There are also at least two switches or control units (116A and 116B) that control electrical connection to three-way valves (FIG. 4). It should be appreciated that during operation, pneumatic device 200 can be placed in idle, expel or aspirate mode (top, middle, and bottom drawings of FIG. 4, respectively) using control unit 400 (or 116A and 116B). As shown in bottom of FIG. 4, when the control unit 400 is placed in aspirate mode, vacuum is created by pneumatic device 200 such that air is pulled through the cell collecting element 104. Control unit 400 can also include an attenuator or a modulator (not shown) such that it can control the amount of vacuum (e.g., aspiration force) and/or positive pressure (e.g., force of expelling) generated within cell collecting element 104. The presence of an attenuator or modulator (not shown) allows a wide variety of pneumatic device 200 to be utilized simply by adjusting the amount of vacuum and pressure generated within cell collecting element 104 using the attenuator/modulator.

As shown in the middle of FIG. 4, cell collecting element 104 can be set to expel mode by allowing the exhaust section of pneumatic device 200 to be operatively connected to cell collecting element 104 thereby creating a greater pressure within cell collecting element 104 relative to the ambient pressure. This increased pressure within cell collecting element 104 causes the cell sample that is located within cell collecting element 104 to be expelled. By placing the open end of cell collecting element 104 into a cell sample preparation or observation vessel, one can transfer the collected cell sample.

The control unit 400 can also be a pedal. Use of a petal as control unit 400 allows the user to control the cell collecting device 100 with his or her foot. While Figures show one pneumatic device 200 for controlling cell collecting device 100 to aspirate or expel, it should be appreciated that two separated pneumatic devices can be used: one for aspiration and the other for expelling collected cells from cell collecting element 104. In addition, as stated above, an attenuator and/or a modulator can also be added to adjust the amount of vacuum and/or exhaust pressure.

When collecting a desired cell sample, the user observes the tissue sample using a dissecting light microscope and contacts or scrapes the desired area of the tissue sample with cell collecting element 104. This scraping action causes separation of cell sample from the tissue sample and is aspirated into cell collecting element 104.

It should be appreciated that the vacuum pressure or the force of aspiration should be sufficient to allow aspiration of separated cell sample into cell collecting element 104 but not too strong as to cause cell sample to be injected into undesired portion of the cell collecting device 100. Typically, the pressure within cell collecting element 104 is ranges from about 5 mmHg to about 100 mmHg, often from about 5 mmHg to about 50 mmHg, and more often about 5 mmHg to about 15 mmHg lower than ambient pressure.

However, it should be appreciated that depending on a particular cell collecting element 104 used, the necessary pressure can vary.

Once the cell sample is collected, the control unit 400 is set to expel mode in order to allow transfer of collected cell sample into a cell sample preparation, storage or observation vessel (not shown). Again, the pressure within cell collecting element 104 should not be too strong to spray the collected sample cells out of the cell sample preparation, storage or observation vessel, but should be strong enough to transfer the collected cell sample from cell collecting element 104 to the cell sample preparation/storage vessel. Typically, the pressure within cell collecting element 104 for expelling the collected cell sample ranges from about 10 mmHg to about 100 mmHg, often from about 20 mmHg to about 75 mmHg, and more often about 30 mmHg to about 40 mmHg higher than ambient pressure. Again, it should be appreciated that depending on a particular cell collecting element 104 used, the necessary pressure can vary.

Referring again to Figures, in some embodiments cell collecting device 100 comprises a cell collecting element 104. Cell collecting element 104 comprises a cell collecting orifice 106 and a pneumatic connector orifice 107, where cell collecting orifice 106 is adapted for aspirating and expelling a cell sample into and from said cell collecting element 104.

The apparatus of the invention also includes a pneumatic connector 128 comprising a first orifice 134 and a second orifice 130. The first orifice 134 of pneumatic connector 128 is removably attached to pneumatic connector orifice 107 of cell collecting element 104.

The apparatus of the invention includes a pneumatic device 200 that is operatively connected to second orifice 130 of pneumatic connector 128. In this manner, cell collecting device 100 is operated by pneumatic device 200. The power box 300 controls and provides electrical power to pneumatic device 200. For a portable unit, power box 300 and pneumatic device 200 can be contained in a single unit.

The apparatus of the invention can also include a control unit 400 operatively connected to pneumatic device 200 such that pneumatic device 200 provides means for aspirating or expelling the cell sample into or from cell collecting element 104 depending on the control unit setting. Control unit 400 is operatively connected to the power unit 300, which control whether pneumatic device 200 is set to aspirate, expel or idle. Control unit 400 can be a separate unit (e.g., as a foot pedal) or can be present within the cell collecting device 100 such as elements 116A and 116B. Having control unit 400 within cell collecting device 100 allows the user to easily control aspiration/expel mode of cell collecting element 104 simply pushing control unit buttons 116A and 116B.

Cell collecting device 100 can also include a guide element 108 adapted to aid in positioning cell collecting element 104 to be removably attached to pneumatic connector 128.

In some embodiments, cell collecting device 100 further comprises a housing 112A and 112B that encases at least a portion of cell collecting element 104. In some instances, control unit is located within housing 112 in the form of control unit buttons 116A and 116B.

Cell collecting device 100 can optionally also include a finger holder 120 such that it aids the user to hold cell collecting device 100 firmly in hand.

Figure 5:
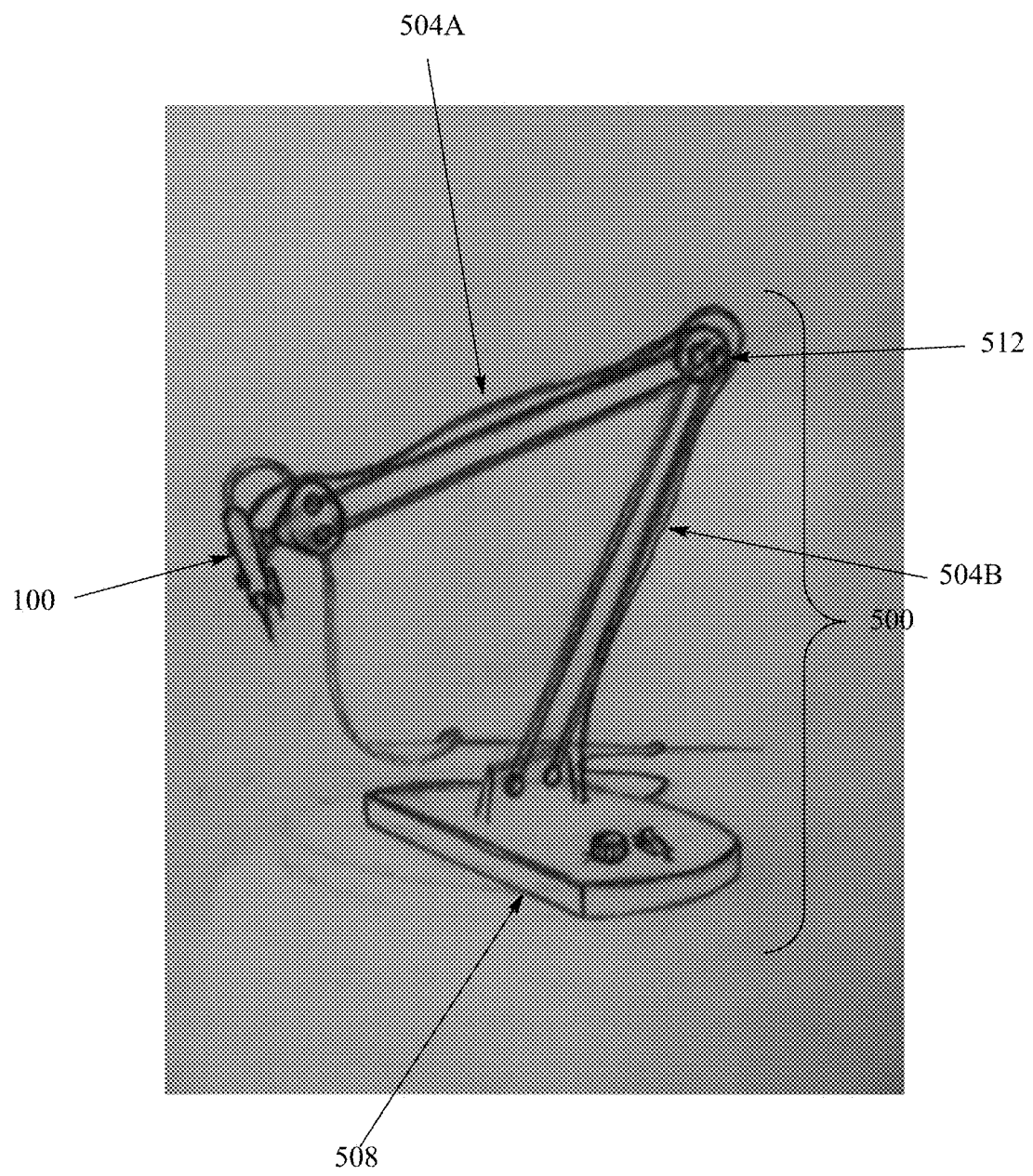
FIG. 5 shows one particular embodiment of a cell collecting device of the invention that is removably attached to a stand comprising a base unit and an arm unit.

Yet in other embodiments, cell collecting device 100 is operatively or removably attached to a stand 500, wherein said stand comprises a base unit 508 and an arm unit 504. Arm unit 504 can comprises a plurality of pieces that are connected by a hinge 512. See FIG. 5.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

FIGURE LEGENDS

100=cell collecting device
104=cell collecting element
106=cell collecting orifice
107=pneumatic connector orifice
108=guide element
112A=Housing (top)
112B=Housing (bottom)
116A and
116B=Control Unit buttons
120=Finger holder
124=Ferrule
128=Pneumatic connector
130=First orifice
134=Second orifice
200=Pneumatic device
300=power box
400=control unit
500=Stand
504A and
504B=Arm Units
508=base unit
512=hinge

EXAMPLES

The cell collection procedure is typically applied in the enrichment of tumor cells from a mixed cell population.

A paraffin fixed tissue sample (or block) determined by prior histological evaluation to contain tumor is sectioned at 10 microns using a microtome. The sections are dehydrated through graded alcohols to water and stained with hematoxylin. The stained slides are dehydrated through graded alcohols to xylene and stored until needed for dissection. For dissection the slides are again dehydrated to water and individual slides are flooded with glycerine. Stained slides are examined under a dissecting microscope and tumor cells identified. Tumor cells are then scraped from the slide under microscopic observation using a pipette drawn to a diameter of approximately 0.1 mm with a pipette puller as a cell collecting element 104. The pipette is attached to a control unit 400 that controls pneumatic device 200 through a power unit 300. The cells scraped from the slide are aspirated into the cell collecting element 104 by setting pneumatic device 200 to aspirate using control unit 400. Cells are then expelled into a molecular preparation tube by switching pneumatic device 200 to expel mode using control unit 400. The obtained cells are washed with appropriate buffers, and DNA or other appropriate molecular product is extracted from the intact cells using a procedure known to one skilled in the art.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus for collecting a cell sample from a tissue sample, said apparatus consisting of:
    a cell sample collecting device comprising a cell collecting element, wherein said cell collecting element comprises a cell collecting orifice and a pneumatic connector orifice, and wherein said cell collecting orifice is adapted for aspirating and expelling a cell sample into and from said cell collecting element, wherein said cell sample collecting device is configured to remove a cell sample from a tissue sample by scraping means;
    a pneumatic connector comprising a first orifice and a second orifice, wherein said first orifice of said pneumatic connector is removably attached to said pneumatic connector orifice of said cell collecting element;
    a pneumatic device operatively connected to said second orifice of said pneumatic connector; and
    a control unit operatively connected to said pneumatic device such that said pneumatic device provides means for aspirating or expelling the cell sample into or from said cell collecting element.

2. The apparatus of claim 1, wherein said cell sample collecting device further comprises a guide element adapted to aid in positioning said cell sample collecting element to be removably attached to said pneumatic connector.

3. The apparatus of claim 1, wherein said cell sample collecting device further comprises a housing that encases at least a portion of said cell sample collecting element.

4. The apparatus of claim 3, wherein said control unit is located within said housing.

5. The apparatus of claim 1, wherein said cell collecting element comprises a pipette.

6. The apparatus of claim 1, wherein said cell collecting device is attached to a stand, wherein said stand comprises a base unit and an arm unit.

7. The apparatus of claim 1, wherein said arm unit comprises a hinge.

8. The apparatus of claim 1, wherein said control unit further comprises a variable control for adjusting the cell sample aspiration force, cell sample expelling force, or both.

9. A method for obtaining a cell sample for analysis from a tissue sample, said method comprising:
    identifying a cell sample to be analyzed from a tissue sample; and
    obtaining the cell sample to be analyzed using an apparatus of claim 1.

10. The method of claim 9, wherein said step of identifying the cell sample to be analyzed comprises observing the tissue sample using a microscope.

11. The method of claim 9, wherein said step of obtaining the cell sample comprises:
    contacting the cell collecting element with the cell sample to be analyzed;
    aspirating the cell sample into said cell collecting element using said pneumatic device; and
    expelling the collected cell sample from said cell collecting element into a cell sample collecting vessel.

12. The method of claim 11 further comprising the step of adjusting the control unit after said step of aspirating the cell sample into said cell collecting element such that said pneumatic device provides a positive pressure within said cell collecting element, thereby expelling the collected cell sample from said cell collecting element.

13. The method of claim 9 further comprising the step of analyzing the obtained cell sample.

* * * * *